United States Patent
Cozic et al.

(10) Patent No.: US 7,148,475 B2
(45) Date of Patent: Dec. 12, 2006

(54) DEVICE FOR AUTOMATED COUPLING BETWEEN A MICRO-CHROMATOGRAPH AND A MASS SPECTROMETER COMPRISING A TEMPERATURE ADJUSTMENT

(75) Inventors: Ronan Cozic, Briis-sous-Forges (FR); Jean-Louis Gass, St. Just Chaleyssin (FR); Jean Bourliaud, Paris (FR)

(73) Assignees: Commissariat a l'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/540,923

(22) PCT Filed: Jan. 9, 2004

(86) PCT No.: PCT/FR2004/050010

§ 371 (c)(1),
(2), (4) Date: Jun. 29, 2005

(87) PCT Pub. No.: WO2004/065956

PCT Pub. Date: Aug. 5, 2004

(65) Prior Publication Data

US 2006/0097148 A1 May 11, 2006

(30) Foreign Application Priority Data

Jan. 14, 2003 (FR) .................................. 03 00343

(51) Int. Cl.
*H01J 49/26* (2006.01)
*B01D 59/44* (2006.01)

(52) U.S. Cl. ...................... 250/288; 250/281; 250/289; 73/23.37; 73/23.42

(58) Field of Classification Search .................... None
See application file for complete search history.

(56) References Cited

U.S. PATENT DOCUMENTS

| 4,501,817 | A | 2/1985 | Andresen et al. |
| 4,662,914 | A | 5/1987 | Hansen et al. |
| 4,970,905 | A | 11/1990 | McClennen et al. |
| 4,988,870 | A | 1/1991 | Diehl |
| 5,281,397 | A | 1/1994 | Ligon et al. |
| 5,424,539 | A | 6/1995 | Brand et al. |
| 6,907,768 | B1 * | 6/2005 | Gass et al. ................. 73/23.37 |

FOREIGN PATENT DOCUMENTS

FR 2 817 347 5/2002

OTHER PUBLICATIONS

Hail, Mark E. et al. "Theoretical and Practical Aspects of Short Open Tubular Columns at Subambient Pressures in Gas Chromatography/Mass Spectrometry" Analytical Chemistry, American Chemical Society, vol. 61, No. 21, pp. 2402-2410, Nov. 1, 1989. XP 000134377.

* cited by examiner

*Primary Examiner*—Nikita Wells
(74) *Attorney, Agent, or Firm*—Oblon, Spivak, McClelland, Maier & Neustadt, P.C.

(57) ABSTRACT

An instrument including a chromatographic column with a final detector and a mass spectrometer. A temperature of an interface including an output tube and a capillary tube adjusting the flow to the spectrometer is adjusted using a leakage flow or pressure sensor outputting data to a control module that adjusts the interface temperature to equalize flows in the tubes.

9 Claims, 3 Drawing Sheets

Figure 1:
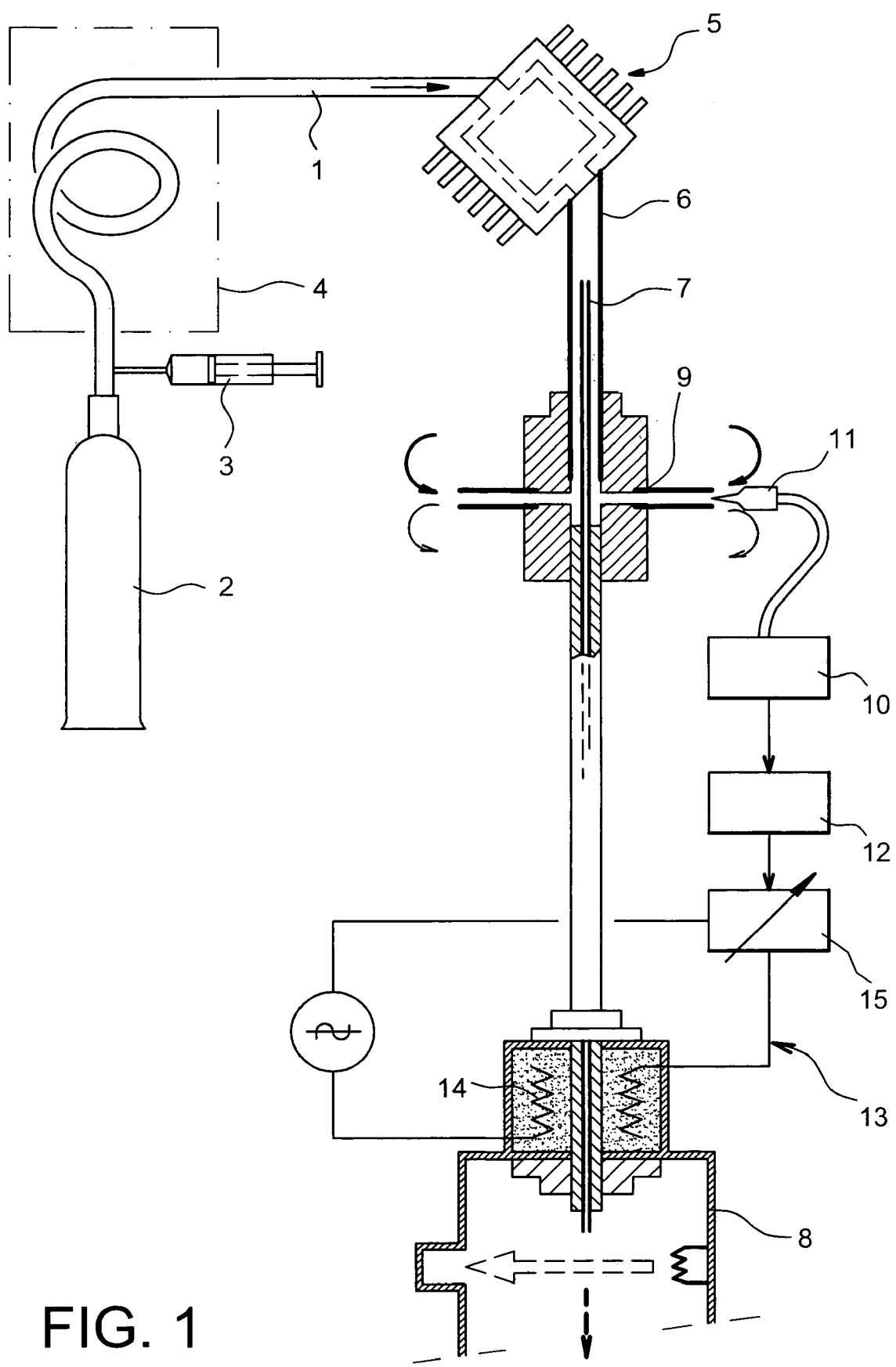

DEVICE FOR AUTOMATED COUPLING BETWEEN A MICRO-CHROMATOGRAPH AND A MASS SPECTROMETER COMPRISING A TEMPERATURE ADJUSTMENT

The invention relates to a coupling device between a chromatograph (or micro-chromatograph) and a mass spectrometer of the type comprising a temperature adjustment at the interface.

It forms an improvement to French patent 2817347 that describes an open type interface, while in some embodiments it may concern slightly different couplings, for example the coupling using the closed type interface. We will briefly describe some considerations extracted from this prior patent to introduce the invention.

The combination of a micro-chromatograph and a mass spectrometer is particularly attractive for carrying out some analyses of gaseous products. However, care has to be taken to maintain suitable operating conditions for these two completely different instruments. Thus, the micro-chromatograph is provided with a detector on the output side such as a katharometer (or a microkatharometer) to record chromatographic peaks by the variation in the composition of the eluate that passes through it. However, this measurement is only correct at constant pressure, for example at atmospheric pressure, but the mass spectrometer operates under a secondary vacuum. Therefore, a determined pressure difference must be produced between the two measurement means when they are close to each other on the instrument, while protecting against operating inequalities particularly due to pumping of the spectrometer and variations of the gas flow passing through the chromatographic column.

In the previous patent, the interface between the chromatograph and the mass spectrometer was open, in other words it communicates with the outside, and the chromatographic column opened up in a capillary tube leading to the mass spectrometer. Communication with the outside provided a means of maintaining a constant pressure at the katharometer. If the flow from the chromatograph was greater than the flow sampled by the spectrometer and imposed by the physical characteristics of the capillary tube, part of the gas eluate was rejected outside the instrument and was lost for the measurement. Otherwise, gas entered the instrument from the outside and into the capillary and participated in the mass spectrometer measurement, distorting it.

The inventors of this prior patent had adjusted the flow in the mass spectrometer and the flow in the chromatograph by adjustable heating at the interface, after observing that heating at the interface reduced the gas flow inlet into the capillary tube of the mass spectrometer, while cooling increased this flow. It was proposed to examine the background noise signal from the mass spectrometer to detect gas entering from outside and to keep this gas quantity as small as possible in order to equalise flows passing through the spectrometer and the chromatograph, as much as possible. If outside air surrounded the instrument and could penetrate into it, it was recommended that peak intensities of water, nitrogen and oxygen in the mass spectrometer should be monitored; an increase in the peaks characteristic of air, in other words the nitrogen and oxygen peaks relative to the peak characteristic of water, was a sign of an entry of air. The operator could then adjust the temperature at the interface to correct the flow accordingly.

Unfortunately, it became apparent that this process could not easily be automated. Therefore the purpose of the invention is to provide a device capable of adjusting flows between the detector of a chromatograph and a mass spectrometer on the output side, as efficiently as in the previous patent but automatically. The proposed solution consists of adopting another measurement to make the temperature adjustment. There are several attractive possibilities based on the measurement of a leak or a pressure at an appropriate location of the instrument.

The pressure is a simple parameter directly correlated to a flow irregularity, and it can therefore by used easily by a usual slaving means while enabling an almost immediate correction. The measurement location will often be at the interface between the chromatograph and the spectrometer, but it can also be elsewhere, further on the output side and particularly at the spectrometer; devices with fairly different appearances could be recommended depending on the nature of the interface (open or closed).

The invention also relates to an analysis device comprising a micro-chromatograph and a mass spectrometer, the output from the micro-chromatograph being connected to the input of the mass spectrometer through an automated coupling device according to the previous definition; and which may also be provided on the input side of the micro-chromatograph with a pre-concentration device based on adsorption followed by a thermal desorption, for example the Airsense® "µTD" pre-concentrator.

The invention will now be described with reference to FIGS. 1, 2 and 3 that show corresponding embodiments of the invention.

FIG. 1 illustrates an instrument on which the invention could be implanted. It comprises a chromatographic column 1 supplied on the input side by a vector gas source or an eluent and by an injector of the product to be analysed or soluted. The chromatographic column 1 is heated to the required temperature in an oven 4. It is known that components of the product to be analysed pass through the column 1 at different speeds depending on their chemical affinity with a specific stationary phase contained in it. A microkatharometer 5 is arranged at the output from the column 1 and measures variations in the gas composition passing through it in a known manner. The column continues as a tube 6 beyond the microkatharometer 5, that usually does not contain any stationary phase and in which the gases can circulate. A capillary tube 7 is housed in the tube 6 and prolongs it as far as a mass spectrometer 8 that makes another measurement on compounds separated by the chromatograph. The tube 6 comprises at least one opening 9 not far from the end of the capillary tube 7 so as to maintain the pressure at the microkatharometer 5 equal to an invariable value, according to the advantage of this open interface between the column 1 and the spectrometer 8. The essential property of the capillary tube 7 is that it only allows passage of a maximum gas flow that depends on the temperature. If the flow output from column 1 is greater, the excess leaks from the tube 6 at the opening 9; otherwise, the surrounding gas enters into the tube 6, then into the capillary tube 7, and ends up in the mass spectrometer 8 if this condition is maintained.

According to one embodiment of the invention, it is intended to place a gas leak detector 10 at the opening 9. It may also include a microkatharometer and operate starting from the difference in thermal conductivity between the ambient gas and the leakage gas. It comprises a suction probe 11 placed at the opening 9. The leak detector LD 228 made by the GL Sciences Company has for example a sensitivity of 0.01 ml per minute, which is sufficient to give good results in the application considered.

Other detectors and particularly flow meters could be envisaged, for example of the Honeywell® "AWN 40000 Series" type, also sensitive to a variation in the thermal conductivity. The advantage is that it is easier to retrieve the measured signal to subsequently control regulation of the interface temperature.

The signal from the detector 10 is input to a control module 12 that acts on a temperature adjustment means 13 of the interface. In a manner similar to the previous patent, this means 13 may consist of an electrical circuit comprising a heating resistance 14 for example located close to the mass spectrometer 8. Preferably, the means 13 must consist of a uniform heating system as long as the maximum length of the capillary tube 7. In this case, it is an adjustable element 15 on which the control module 12 acts as a function of the signal from the detector 10. The control module 12 may comprise an electronic card or an analogue calibration means giving an adjustment of the element 15 as a function of the received signal expressing the difference with a required state.

Figure 2:
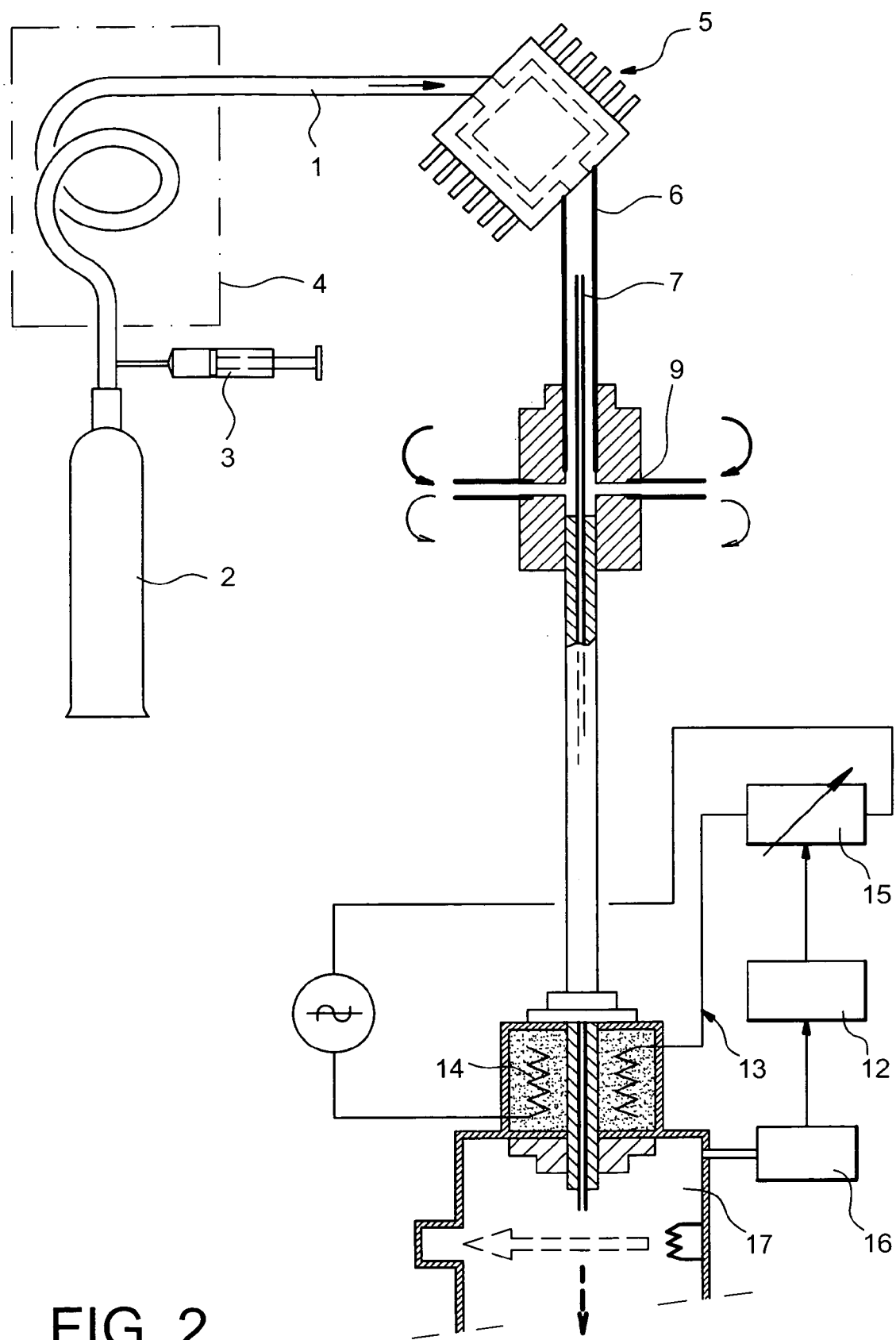

FIG. 2 illustrates another embodiment similar to the previous embodiment, except that the detector 10 is replaced by another pressure detector 16 connected to the chamber 17 of the mass spectrometer 8. In a known manner, for example the Hewlett-Packard® "HP59864" ionisation gauge, can be used to estimate the pressure in the chamber 17 starting from the air density measured in the mass spectrometer. The detector 16 inputs data to the control module 12 in the same way as the previous detector 10, while the remainder of the instrument remains unchanged. It was found to be perfectly possible to adjust the heating at the interface using the pressure in the chamber 17. In this embodiment, the interface remains open.

Figure 3:
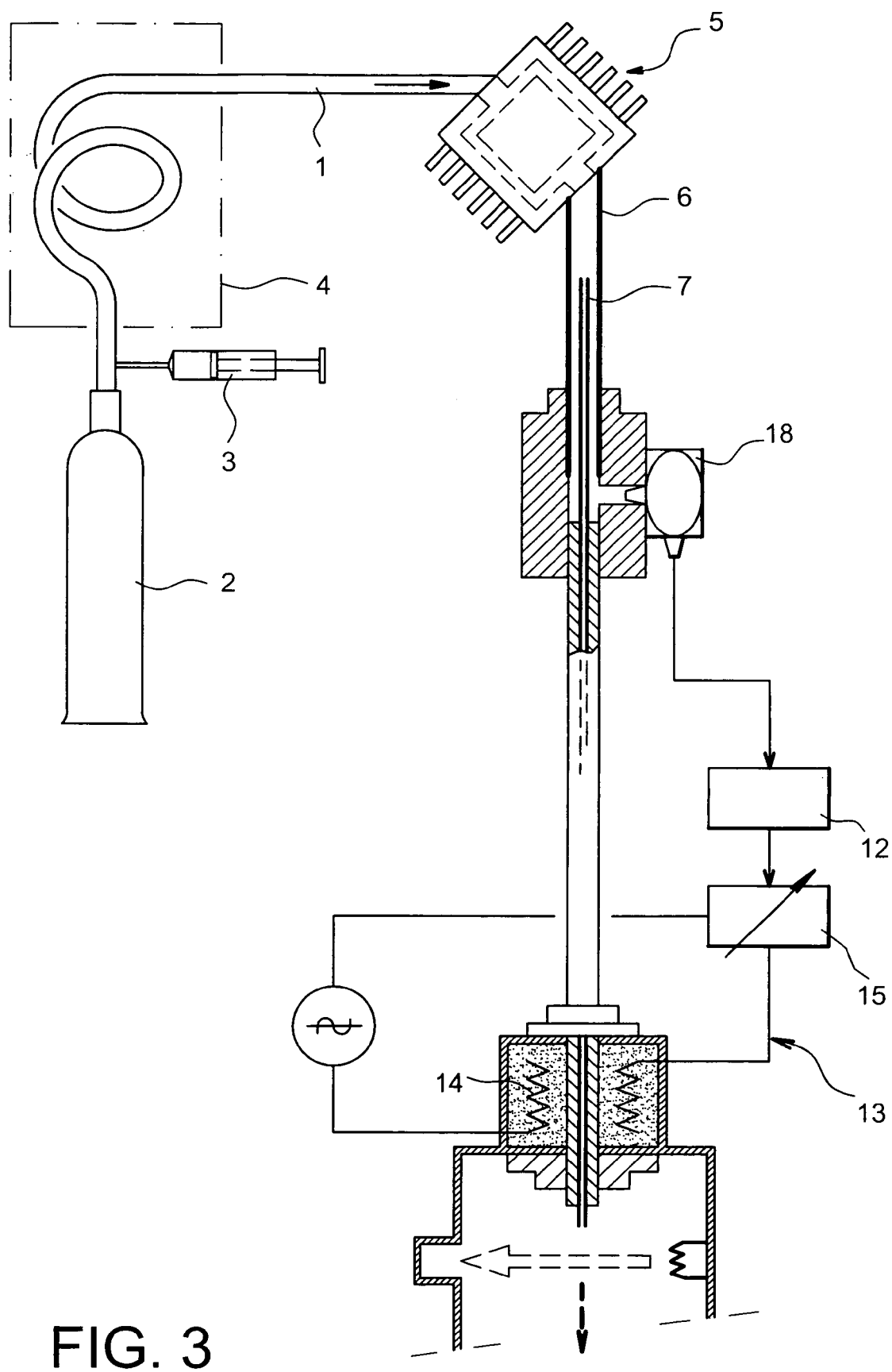

FIG. 3 illustrates a closed interface. The tube 6 no longer communicates with the outside, such that the only outlet for the eluate is the capillary tube 7. The closed interface was not considered in the previous patent, but improvements in this patent can be applied to it. For example a pressure sensor 18, for example the Sensor Technics® "HCX Series" sensor could be fitted at the end of the tube 6 to measure the pressure of eluate in it, and to slave it to a fixed value that guarantees that flows will be equal. Once again, the interface temperature is controlled by the control module 12 and the electrical heating circuit.

The invention claimed is:

1. A coupling device between a chromatograph and a mass spectrometer, comprising:
   a closed interface between a final detector of the chromatograph and the spectrometer, the interface comprising:
      a tube coming out of the chromatograph into which a capillary tube leading to the spectrometer is pushed, and
      a temperature adjustment device; and
   a pressure sensor in the capillary tube coming out of the chromatograph, through which a control module controlling the temperature adjustment device receives data.

2. An analysis device comprising:
   a micro-chromatograph and a mass spectrometer, an output from the micro-chromatograph being connected to an input to the mass spectrometer through an automated coupling device according to claim 1.

3. An analysis device according to claim 2, further comprising a pre-concentration device on an input side of the micro-chromatograph based on adsorption followed by a thermal desorption.

4. A coupling device between a chromatograph and a mass spectrometer, comprising:
   an open interface between a final detector of the chromatograph and the spectrometer, the interface comprising:
      a tube coming out of the chromatograph into which a capillary tube leading to the spectrometer is pushed, and
      a temperature adjustment device; and
   a flow sensor or a leak detector through the capillary tube coming out of the chromatograph, through which a control module controlling the temperature adjustment device receives data.

5. An analysis device comprising:
   a micro-chromatograph and a mass spectrometer, an output from the micro-chromatograph being connected to an input to the mass spectrometer through an automated coupling device according to claim 4.

6. An analysis device according to claim 5, further comprising a pre-concentration device on an input side of the micro-chromatograph based on adsorption followed by a thermal desorption.

7. A coupling device between a chromatograph and a mass spectrometer, comprising:
   an open interface between a final detector of the chromatograph and the spectrometer, the interface comprising:
      a tube coming out of the chromatograph into which a capillary tube leading to the spectrometer is pushed; and
      a temperature adjustment device; and
   a pressure sensor in a chamber of the mass spectrometer, through which a control module controlling the temperature adjustment means receives data.

8. An analysis device comprising:
   a micro-chromatograph and a mass spectrometer, an output from the micro-chromatograph being connected to an input to the mass spectrometer through an automated coupling device according to claim 7.

9. An analysis device according to claim 8, further comprising a pre-concentration device on an input side of the micro-chromatograph based on adsorption followed by a thermal desorption.

* * * * *